US007959762B2

(12) United States Patent
Weerawarna

(10) Patent No.: US 7,959,762 B2
(45) Date of Patent: Jun. 14, 2011

(54) METHOD FOR MAKING BIODEGRADABLE SUPERABSORBENT PARTICLES

(75) Inventor: S Ananda Weerawarna, Seattle, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 302 days.

(21) Appl. No.: 12/165,015

(22) Filed: Jun. 30, 2008

(65) Prior Publication Data

US 2009/0321029 A1    Dec. 31, 2009

(51) Int. Cl.
D21H 13/04    (2006.01)
D01D 5/06    (2006.01)

(52) U.S. Cl. ............. 162/157.6; 264/140; 264/141; 264/180; 264/183; 264/186; 264/187; 264/211.11; 264/211.16; 264/211.19; 428/359; 428/402; 604/374; 604/375; 604/376; 604/910

(58) Field of Classification Search .......... 162/146, 162/157.6; 264/109, 115, 118, 122, 140, 264/141, 142, 144, 145, 163, 180, 183, 186, 264/187, 211.18, 211.11, 211.16, 211.19; 536/97, 98; 428/359, 402; 604/374, 375, 604/376, 910
See application file for complete search history.

(56) References Cited

U.S. PATENT DOCUMENTS

| | | |
|---|---|---|
| 3,645,836 A | 2/1972 | Torr |
| 4,028,290 A | 6/1977 | Reid |
| 4,128,692 A | 12/1978 | Reid |
| 4,143,163 A | 3/1979 | Hutchinson et al. |
| 4,273,118 A | 6/1981 | Smith |
| 4,319,956 A | 3/1982 | Snyder et al. |
| 4,497,930 A | 2/1985 | Yamasaki et al. |
| 4,605,401 A | 8/1986 | Chemilir et al. |
| 4,624,868 A | 11/1986 | Muller |
| 4,693,713 A | 9/1987 | Chmelir |
| 4,952,550 A | 8/1990 | Wallach et al. |
| 4,959,341 A | 9/1990 | Wallach |
| 4,966,694 A | 10/1990 | Namikoshi et al. |
| 5,231,122 A | 7/1993 | Palumbo et al. |
| 5,384,179 A | 1/1995 | Roe et al. |
| 5,425,725 A | 6/1995 | Tanzer et al. |
| 5,470,964 A | 11/1995 | Qin |
| 5,498,705 A | 3/1996 | Qin |
| 5,550,189 A | 8/1996 | Qin et al. |
| 5,612,411 A | 3/1997 | Gross |
| 5,688,776 A | 11/1997 | Bauer et al. |
| 5,736,595 A | 4/1998 | Gunther et al. |
| 5,801,116 A | 9/1998 | Cottrell et al. |
| 5,847,031 A | 12/1998 | Klimmek et al. |
| 6,051,317 A | 4/2000 | Brueggemann et al. |
| 6,162,541 A | 12/2000 | Chou et al. |
| 6,288,158 B1 | 9/2001 | Schapowalov et al. |
| 6,296,936 B1 | 10/2001 | Yahiaoui et al. |
| 6,331,619 B1 | 12/2001 | Besemer et al. |
| 6,339,039 B1 | 1/2002 | Porath et al. |
| 6,387,978 B2 | 5/2002 | Ronan et al. |
| 6,436,508 B1 | 8/2002 | Ciammaichella et al. |
| 6,524,348 B1 | 2/2003 | Jewell et al. |
| 6,562,743 B1 | 5/2003 | Cook et al. |
| 6,689,934 B2 | 2/2004 | Dodge, II et al. |
| 6,713,460 B2 | 3/2004 | Huppe |
| 6,730,722 B1 | 5/2004 | Eck et al. |
| 6,765,042 B1 | 7/2004 | Thornton et al. |
| 6,846,924 B1 | 1/2005 | Malmgren et al. |
| 6,998,367 B2 | 2/2006 | Qin |
| 7,153,904 B2 | 12/2006 | Richardson et al. |
| 7,306,039 B2 | 12/2007 | Wang et al. |
| 7,321,007 B2 | 1/2008 | Gagliardi et al. |
| 7,407,912 B2 | 8/2008 | Mertens et al. |
| 7,615,579 B2 | 11/2009 | Joy et al. |
| 2003/0027787 A1 | 2/2003 | Couture |
| 2003/0068944 A1 | 4/2003 | Carlucci et al. |
| 2003/0144642 A1 | 7/2003 | Dopps et al. |
| 2003/0232965 A1 | 12/2003 | Bergeron |
| 2004/0024092 A1 | 2/2004 | Sorens et al. |
| 2004/0157734 A1 | 8/2004 | Mertens et al. |
| 2004/0214499 A1 | 10/2004 | Qin et al. |
| 2004/0236260 A1 | 11/2004 | Griffiths et al. |
| 2005/0153123 A1 | 7/2005 | Herfeft et al. |
| 2005/0155491 A1 | 7/2005 | Faust et al. |
| 2005/0214541 A1 | 9/2005 | Berrada et al. |
| 2006/0142477 A1 | 6/2006 | Glasser |
| 2006/0147689 A1 | 7/2006 | Wallajapet et al. |
| 2006/0165762 A1 | 7/2006 | Plaut et al. |
| 2007/0093907 A1 | 4/2007 | Goupil et al. |
| 2007/0179291 A1 | 8/2007 | Thibodeau et al. |
| 2008/0009616 A1 | 1/2008 | Frank et al. |
| 2008/0078514 A1 | 4/2008 | Weerawarna et al. |
| 2008/0078515 A1 | 4/2008 | Weerawarna et al. |
| 2008/0079187 A1 | 4/2008 | Weerawarna et al. |
| 2008/0079188 A1 | 4/2008 | Weerawarna et al. |
| 2008/0081165 A1 | 4/2008 | Weerawarna et al. |
| 2008/0081189 A1 | 4/2008 | Weerawarna et al. |
| 2008/0081190 A1 | 4/2008 | Weerawarna et al. |
| 2008/0081191 A1 | 4/2008 | Weerawarna et al. |
| 2008/0081843 A1 | 4/2008 | Weerawarna et al. |
| 2008/0082064 A1 | 4/2008 | Luo et al. |
| 2008/0082065 A1 | 4/2008 | Weerawarna et al. |
| 2008/0082066 A1 | 4/2008 | Luo et al. |
| 2008/0082067 A1 | 4/2008 | Weerawarna et al. |
| 2008/0082069 A1 | 4/2008 | Qin et al. |
| 2008/0314537 A1 | 12/2008 | Weerawarna et al. |
| 2009/0321029 A1 | 12/2009 | Weerawarna |
| 2009/0321030 A1 | 12/2009 | Weerawarna |
| 2009/0325799 A1 | 12/2009 | Weerawarna |
| 2009/0325800 A1 | 12/2009 | Weerawarna |

FOREIGN PATENT DOCUMENTS

| | | |
|---|---|---|
| WO | WO 00/21581 | 4/2000 |
| WO | WO 2005/123781 | 12/2005 |
| WO | 2006/079221 A1 | 8/2006 |
| WO | WO 2006/079221 | 8/2006 |
| WO | 2006/119638 A1 | 11/2006 |
| WO | WO 2006/119638 | 11/2006 |

OTHER PUBLICATIONS

Final Office Action, Notification Date Apr. 5, 2011, U.S. Appl. No. 12/165,075, filed Jun. 30, 2008, First Named Inventor: S. Ananda Weerawarna.

*Primary Examiner* — Eric Hug
*Assistant Examiner* — Peter Chin
(74) *Attorney, Agent, or Firm* — John M. Crawford

(57) ABSTRACT

A method for making mixed polymer composite fibers in which a carboxyalkyl cellulose and a starch are blended in water to provide an aqueous gel; the aqueous gel treated with a first crosslinking agent to provide a crosslinked gel; the crosslinked gel mixed with a water-miscible solvent to provide fibers; and the fibers treated with a second crosslinking agent to provide crosslinked mixed polymer composite fibers.

19 Claims, 2 Drawing Sheets

METHOD FOR MAKING BIODEGRADABLE SUPERABSORBENT PARTICLES

BACKGROUND OF THE INVENTION

Personal care absorbent products, such as infant diapers, adult incontinent pads, and feminine care products, typically contain an absorbent core that includes superabsorbent polymer particles distributed within a fibrous matrix. Superabsorbents are water-sweltable, generally water-insoluble absorbent materials having a high absorbent capacity for body fluids. Superabsorbent polymers (SAPs) in common use are mostly derived from acrylic acid, which is itself derived from petroleum oil, a non-renewable raw material. Acrylic acid polymers and SAPs are generally recognized as not being biodegradable. Despite their wide use, some segments of the absorbent products market are concerned about the use of non-renewable petroleum oil-derived materials and their non-biodegradable nature. Acrylic acid based polymers also comprise a meaningful portion of the cost structure of diapers and incontinent pads. Users of SAP are interested in lower cost SAPs. The high cost derives in part from the cost structure for the manufacture of acrylic acid which, in turn, depends upon the fluctuating price of petroleum oil. Also, when diapers are discarded after use they normally contain considerably less than their maximum or theoretical content of body fluids. In other words, in terms of their fluid holding capacity, they are "over-designed". This "over-design" constitutes an inefficiency in the use of SAP. The inefficiency results in part from the fact that SAPs are designed to have high gel strength (as demonstrated by high absorbency under load or AUL). The high gel strength (upon swelling) of currently used SAP particles helps them to retain a lot of void space between particles, which is helpful for rapid fluid uptake. However, this high "void volume" simultaneously results in there being a lot of interstitial (between particle) liquid in the product in the saturated state. When there is a lot of interstitial liquid the "rewet" value or "wet feeling" of an absorbent product is compromised.

In personal care absorbent products, U.S. southern pine fluff pulp is commonly used in combination with the SAP. This fluff is recognized worldwide as the preferred fiber for absorbent products. The preference is based on the fluff pulp's advantageous high fiber length (about 2.8 mm) and its relative ease of processing from a wetland pulp sheet to an airlaid web. Fluff pulp is also made from renewable and biodegradable cellulose pulp fibers. Compared to SAP, these fibers are inexpensive on a per mass basis, but tend to be more expensive on a per unit of liquid held basis. These fluff pulp fibers mostly absorb within the interstices between fibers. For this reason, a fibrous matrix readily releases acquired liquid on application of pressure. The tendency to release acquired liquid can result in significant skin wetness during use of an absorbent product that includes a core formed exclusively from cellulosic fibers. Such products also tend to leak acquired liquid because liquid is not effectively retained in such a fibrous absorbent core.

Superabsorbent produced in fiber form has a distinct advantage over particle forms in some applications. Such superabsorbent fiber can be made into a pad form without added non-superabsorbent fiber. Such pads will also be less bulky due to elimination or reduction of the non superabsorbent fiber used, Liquid acquisition will be more uniform compared to a fiber pad with shifting superabsorbent particles.

A need therefore exists for a fibrous superabsorbent material that is simultaneously made from a biodegradable renewable resource like cellulose that is inexpensive. In this way, the superabsorbent material can be used in absorbent product designs that are efficient. These and other objectives are accomplished by the invention set forth below.

SUMMARY OF THE INVENTION

The present invention provides a method for making mixed polymer composite fibers. In the method, a carboxyalkyl cellulose and a starch are blended in water to provide an aqueous gel; the aqueous gel is treated with a first crosslinking agent to provide a crosslinked gel; the crosslinked gel is mixed with a water-miscible solvent to provide fibers; and the fibers are treated with a second crosslinking agent to provide crosslinked mixed polymer composite fibers.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
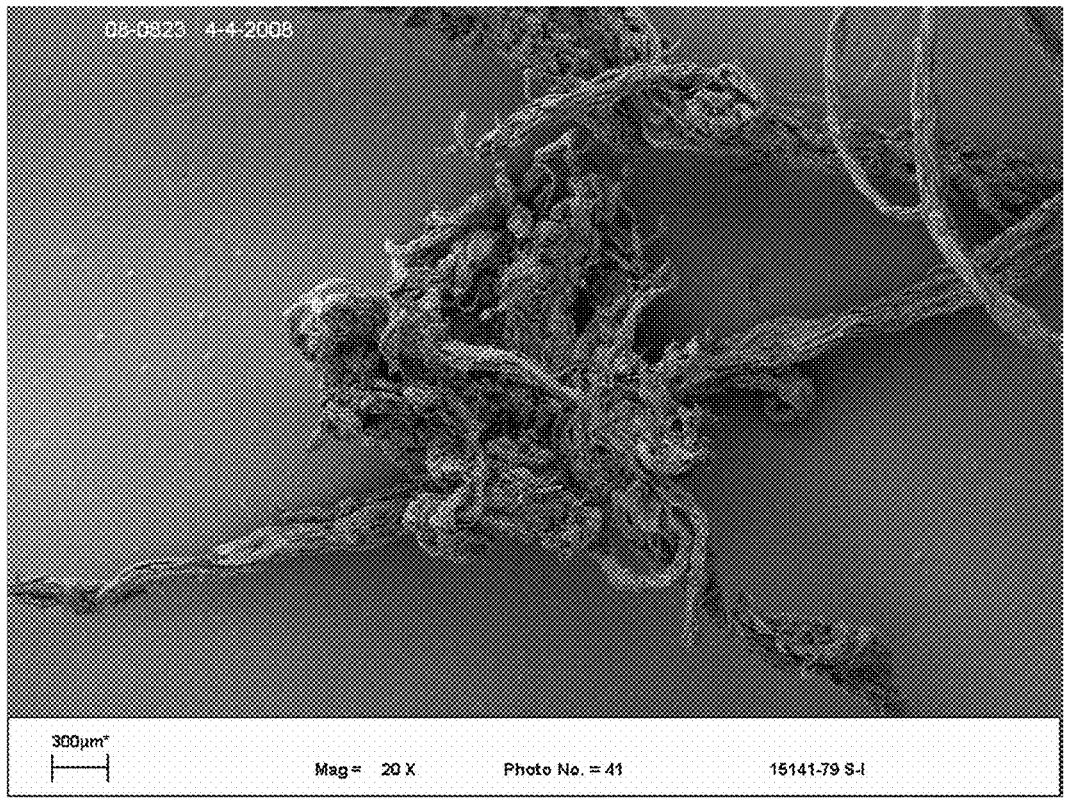
FIG. 1 is a scanning electron microscope photograph (20×) of representative mixed polymer composite fibers formed in accordance with the method of the invention.

The present invention provides a method for making mixed polymer composite fibers. In the method, a carboxyalkyl cellulose and a starch are blended in water to provide an aqueous gel; the aqueous gel treated with a first crosslinking agent to provide a crosslinked gel; the crosslinked gel mixed with a water-miscible solvent to provide fibers; and the fibers treated with a second crosslinking agent to provide crosslinked mixed polymer composite fibers.

The mixed polymer composite fiber is a fiber comprising a carboxyalkyl cellulose and a starch. The carboxyalkyl cellulose, which is mainly in the sodium salt form, can be in other salt forms such as potassium and ammonium forms. The mixed polymer composite fiber is formed by intermolecular crosslinking of mixed polymer molecules, and is water insoluble and water swellable.

As used herein, the term "mixed polymer composite fiber" refers to a fiber that is the composite of two different polymer molecules (i.e., mixed polymer molecules). The mixed polymer composite fiber is a homogeneous composition that includes two associated polymers: (1) a carboxyalkyl cellulose and (2) a starch.

The carboxyalkyl cellulose useful in making the mixed polymer composite fiber has a degree of carboxyl group substitution (DS) of from about 0.3 to about 2.5. In one embodiment, the carboxyalkyl cellulose has a degree of carboxyl group substitution of from about 0.5 to about 1.5.

Although a variety of carboxyalkyl celluloses are suitable for use in making the mixed polymer composite fiber, in one embodiment, the carboxyalkyl cellulose is carboxymethyl cellulose. In another embodiment, the carboxyalkyl cellulose is carboxyethyl cellulose.

The carboxyalkyl cellulose is present in the mixed polymer composite fiber in an amount from about 60 to about 99% by weight based on the weight of the mixed polymer composite fiber. In one embodiment, the carboxyalkyl cellulose is present in an amount from about 80 to about 95% by weight based on the weight of the mixed polymer composite fiber. In addition to carboxyalkyl cellulose derived from wood pulp containing some carboxyalkyl hemicellulose, carboxyalkyl cellulose derived from non-wood pulp, such as cotton linters, is suitable for preparing the mixed polymer composite fiber. For carboxyalkyl cellulose derived from wood products, the mixed polymer fibers include carboxyalkyl hemicellulose in an amount up to about 20% by weight based on the weight of the mixed polymer composite fiber. Suitable carboxyalkyl celluloses include carboxyalkyl celluloses (carboxymethyl cellulose) obtained from commercial sources.

In addition to a carboxyalkyl cellulose, the mixed polymer composite fiber includes a starch. Starches are composed of two polysaccharides: amylose and amylopectin. Amylose is a linear polysaccharide having an average molecular weight of about 250,000 g/mole. Amylopectin is a branched polysaccharide (branching via 1,6-α-glucosidic links) having an average molecular weight of about 75,000,000 g/mole. Typically, the ratio of amylose to amylopectin is from about 1:4 to about 1:5.

Starches suitable for use in the present invention may be obtained from corn, wheat, maize, rice, sorghum, potato, cassava, barley, buckwheat, millet, oat, arrowroot, beans, peas, rye, tapioca, sago, and amaranth. Also suitable are waxy starches, such as from corn, wheat, maize, rice, sorghum, potato, cassava, and barley. Mixtures of starches can also be used.

Suitable starches for use in the invention include cooked and pre-gelatinized starches. Certain cooked and pre-gelatinized starches are commercially available from a variety of commercial sources.

Starch is present in the fiber in an amount from about 1 to about 20% by weight based on the weight of the mixed polymer composite fiber. In one embodiment, starch is present in an amount from about 1 to about 15% by weight based on the weight of the mixed polymer composite fiber. In one embodiment, starch is present in an amount from about 2 to about 15% by weight based on the weight of the mixed polymer composite fiber. In certain embodiments, starch is present in an amount from about 4 to about 8% by weight based on the weight of the mixed polymer composite fiber.

The preparation of the mixed polymer composite fiber is a multistep process. In one embodiment, the starch is first cooked in water (e.g., 75° C. for 45 min). Then, an aqueous solution of a carboxyalkyl cellulose is added to the aqueous starch. A first crosslinking agent is added and mixed to obtain a mixed polymer composite gel (crosslinked gel) formed by intermolecular crosslinking of water-soluble polymers.

Suitable first crosslinking agents include crosslinking agents that are reactive towards hydroxyl groups and carboxyl groups. Representative crosslinking agents include metallic crosslinking agents, such as aluminum (III) compounds, titanium (IV) compounds, bismuth (III) compounds, boron (III) compounds, and zirconium (IV) compounds. The numerals in parentheses in the preceding list of metallic crosslinking agents refers to the vatency of the metal.

The mixed polymer composite fiber is generated by rapid mixing of the mixed polymer composite gel with a water-miscible solvent. This fiber generated after first crosslinking has a high level of sliminess when hydrated and forms soft gels. Therefore this fiber cannot be used in absorbent applications without further treatment. The mixed polymer composite fiber thus obtained is further crosslinked (e.g., surface crosslinked) by treating with a second crosslinking agent in a water-miscible solvent containing water. The composition of water-miscible solvent and water is such that the fiber does not change its fiber form and return to gel state. The second crosslinking agent can be the same as or different from the first crosslinking agent.

The mixed polymer fibers are substantially insoluble in water while being capable of absorbing water. The fibers are rendered water insoluble by virtue of a plurality of non-permanent intra-fiber metal crosslinks. As used herein, the term "non-permanent intra-fiber metal crosslinks" refers to the nature of the crosslinking that occurs within individual modified fibers of the invention (i.e., intra-fiber) and among and between each fiber's constituent polymer molecules.

The fibers are intra-fiber crosslinked with metal crosslinks. The metal crosslinks arise as a consequence of an associative interaction (e.g., bonding) between functional groups (e.g., carboxy, carboxylate, or hydroxyl groups) of the fiber's polymers and a multi-valent metal species. Suitable multi-valent metal species include metal ions having a valency of three or greater and that are capable of forming associative interpolymer interactions with functional groups of the polymer molecules (e.g., reactive toward associative interaction with the carboxy, carboxylate, or hydroxyl groups). The polymers are crosslinked when the multi-valent metal species form associative interpolymer interactions with functional groups on the polymers. A crosslink may be formed intramolecularly within a polymer or may be formed intermolecularly between two or more polymer molecules within a fiber. The extent of intermolecular crosslinking affects the water solubility of the composite fibers (i.e., the greater the crosslinking, the greater the insolubility) and the ability of the fiber to swell on contact with an aqueous liquid.

The fibers include non-permanent intrafiber metal crosslinks formed both intermolecularly and intramolecularly in the population of polymer molecules. As used herein, the term "non-permanent crosslink" refers to the metal crosslink formed with two or more functional groups of a polymer molecule (intramolecularly) or formed with two or more functional groups of two or more polymer molecules (intermolecularly). It will be appreciated that the process of dissociating and re-associating (breaking and reforming crosslinks) the multi-valent metal ion and polymer molecules is dynamic and also occurs during liquid acquisition. During water acquisition the individual fibers and fiber bundles swell and change to gel state. The ability of non-permanent metal crosslinks to dissociate and associate under water acquisition imparts greater freedom to the gets to expand than if the gel was restrictively crosslinked by permanent crosslinks that do not have the ability to dissociate and re-associate. Covalent organic crosslinks, such as ether crosslinks, are permanent crosslinks that do not dissociate and re-associate.

The fibers have fiber widths of from about 2 μm to about 50 μm (or greater) and coarseness that varies from soft to rough.

Figure 2:
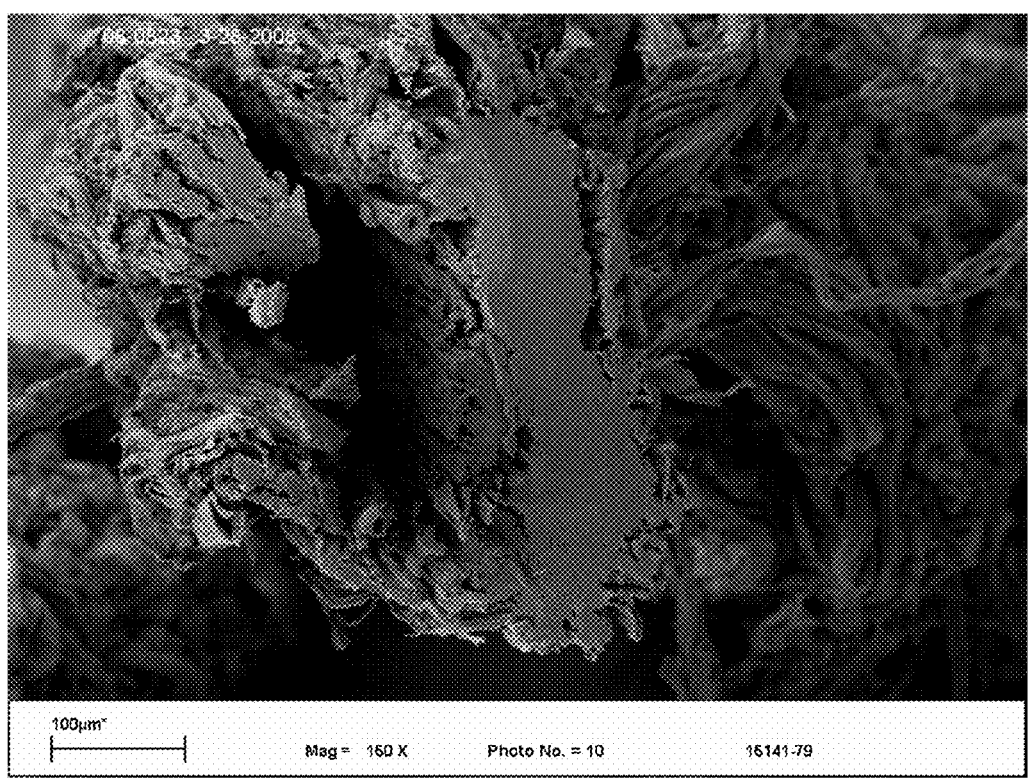
FIG. 2 is a scanning electron microscope photograph (150×) of representative mixed polymer composite fibers formed in accordance with the method of the invention.

Representative mixed polymer composite fibers are illustrated in FIGS. 1 and 2. FIG. 1 is a scanning electron microscope photograph (20×) of representative mixed polymer composite fibers formed in accordance with the method of the invention (Sample 5, Table 1). FIG. 2 is a scanning electron microscope photograph (150×) of representative mixed polymer composite fibers formed in accordance with the method of the invention (Sample 5, Table 1).

The fibers are highly absorptive fibers. The fibers have a Free Swell Capacity of from about 30 to about 60 g/g (0.9% saline solution) and a Centrifuge Retention Capacity (CRC) of from about 15 to about 40 g/g (0.9% saline solution).

The fibers can be formed into pads by conventional methods including air-laying techniques to provide fibrous pads having a variety of liquid wicking characteristics. For example, pads absorb liquid at a rate of from about 10 ml/sec to about 0.005 ml/sec (0.9% saline solution/10 ml application). The integrity of the pads can be varied from soft to very strong.

The mixed polymer composite fibers are water insoluble and water swellable. Water insolubility is imparted to the fiber by intermolecular crosslinking of the mixed polymer molecules, and water swellability is imparted to the fiber by the presence of carboxylate anions with associated cations. The fibers are characterized as having a relatively high liquid absorbent capacity for water (e.g., pure water or aqueous solutions, such as salt solutions or biological solutions such as urine). Furthermore, because the mixed polymer fiber has the structure of a fiber, the mixed polymer composite fiber also possesses the ability to wick liquids. The mixed polymer composite fibers advantageously have dual properties of high liquid absorbent capacity and liquid wicking capacity.

Mixed polymer fibers having slow wicking ability of fluids are useful in medical applications, such as wound dressings and others. Mixed polymer fibers having rapid wicking capacity for urine are useful in personal care absorbent product applications. The mixed polymer fibers can be prepared having a range of wicking properties from slow to rapid for water and 0.9% aqueous saline solutions.

The mixed polymer composite fibers are useful as superabsorbents in personal care absorbent products (e.g., infant diapers, feminine care products and adult incontinence products). Because of their ability to wick liquids and to absorb liquids, the mixed polymer composite fibers are useful in a variety of other applications, including, for example, wound dressings, cable wrap, absorbent sheets or bags, and packaging materials.

In one aspect of the invention, methods for making mixed polymer composite fibers are provided. In the methods, the mixed polymer composite fibers are generated from solution and formed into fibers during the solvent exchange process under shear mixing conditions. As noted above, fiber formation results from shear mixing the crosslinked gel with the water-miscible solvent and effects solvent exchange and generation of composite fiber in the resultant mixed solvent.

In one embodiment, the method for making the mixed polymer composite fibers (crosslinked fibers) includes the steps of: (a) blending a carboxyalkyl cellulose (e.g., mainly salt form) and a starch in water to provide an aqueous gel; (b) treating the aqueous gel with a first crosslinking agent to provide a crosslinked gel; (c) mixing the crosslinked gel with a water-miscible solvent to provide fibers; and (d) treating the fibers with a second crosslinking agent (e.g., surface crosslinking) to provide mixed polymer composite fibers. The mixed polymer composite fibers so prepared can be fiberized and dried.

In the process, a carboxyalkyl cellulose and a starch are blended in water to provide an aqueous gel.

Suitable carboxyalkyl celluloses have a degree of carboxyl group substitution of from about 0.3 to about 2.5, and in one embodiment have a degree of carboxyl group substitution of from about 0.5 to about 1.5. In one embodiment, the carboxyalkyl cellulose is carboxymethyl cellulose. The aqueous gel includes from about 60 to about 99% by weight carboxyalkyl cellulose based on the weight of the product mixed polymer composite fiber. In one embodiment, the aqueous gel includes from about 80 to about 95% by weight carboxyalkyl cellulose based on the weight of mixed polymer composite fiber.

In the method, the aqueous gel including the carboxyalkyl cellulose and starch is treated with a suitable amount of a first crosslinking agent to provide a crosslinked gel.

Suitable first crosslinking agents include crosslinking agents that are reactive towards hydroxyl groups and carboxyl groups. Representative crosslinking agents include metallic crosslinking agents, such as aluminum (III) compounds, titanium (IV) compounds, bismuth (III) compounds, boron (III) compounds, and zirconium (IV) compounds. The numerals in parentheses in the preceding list of metallic crosslinking agents refers to the valency of the metal.

Representative metallic crosslinking agents include aluminum sulfate; aluminum hydroxide; dihydroxy aluminum acetate (stabilized with boric acid); other aluminum salts of carboxylic acids and inorganic acids; other aluminum complexes, such as Ultrion 8186 from Nalco Company (aluminum chloride hydroxide); boric acid; sodium metaborate; ammonium zirconium carbonate; zirconium compounds containing inorganic ions or organic ions or neutral ligands; bismuth ammonium citrate; other bismuth salts of carboxylic acids and inorganic acids; titanium (IV) compounds, such as titanium (IV) bis(triethylaminato) bis(isopropoxide) (commercially available from the Dupont Company under the designation Tyzor TE); and other titanates with alkoxide or carboxylate ligands.

The first crosslinking agent is effective for associating and crosslinking the carboxyalkyl cellulose (with or without carboxyalkyl hemicellulose) and starch molecules. The first crosslinking agent is applied in an amount of from about 0.1 to about 20% by weight based on the total weight of the mixed polymer composite fiber. The amount of first crosslinking agent applied to the polymers will vary depending on the crosslinking agent. In general, the fibers have an aluminum content of about 0.04 to about 0.8% by weight based on the weight of the mixed polymer composite fiber for aluminum crosslinked fibers, a titanium content of about 0.10 to about 1.5% by weight based on the weight of the mixed polymer composite fiber for titanium crosslinked fibers, a zirconium content of about 0.09 to about 2.0% by weight based on the weight of the mixed polymer composite fiber for zirconium crosslinked fibers, and a bismuth content of about 0.90 to about 5.0% by weight based on the weight of the mixed polymer composite fiber for bismuth crosslinked fibers.

The crosslinked gel formed by treating the aqueous gel of a carboxyalkyl cellulose and a starch with a first crosslinking agent is then mixed with a water-miscible solvent to provide fibers. Suitable water-miscible solvents include water-miscible alcohols and ketones. Representative water-miscible solvents include acetone, methanol, ethanol, isopropanol, and mixtures thereof. In one embodiment, the water-miscible solvent is ethanol. In another embodiment, the water-miscible solvent is isopropanol.

The volume of water-miscible solvent added to the gel ranges from about 1:1 to about 1:5 water (the volume used in making the aqueous gel of carboxyalkyl cellulose and starch) to water-miscible solvent.

In the method, mixing the crosslinked gel with the water-miscible solvent includes stirring to provide fibers. The mixing step and the use of the water-miscible solvent controls the rate of dehydration and solvent exchange and provides for fiber formation. Mixing can be carried out using a variety of devices including overhead stirrers, Hobart mixers, British disintegrators, and blenders. For these mixing devices, the blender provides the greatest shear and the overhead stirrer provides the least shear. As noted above, fiber formation results from mixing with the water-miscible solvent and effects solvent exchange and dehydration. The nature of fiber produced by the mixing step can be controlled by the type of mixer, rate of mixing, and the percent solids in water (i.e., the amount of carboxyalkyl cellulose and starch present in the crosslinked gel prior to addition of the water-miscible solvent).

For 1% solids in water, overhead mixers and stirrers including, for example, spiral mixers, provide relatively coarse fibers. These fibers may have the form of shredded paper. Fine fibers are produced using high shear devices, such as a blender (high speed Waring blender). These fine fibers have the appearance of disintegrated cotton fibers. In use, coarse fibers are advantageous for wicking and for avoiding gel blocking during water acquisition and change of fiber form to gel form. Fine fibers are subject to gel blocking, which results from fibers swelling and the collapse of interstitial channels useful for liquid wicking during water acquisition and change of fiber form to gel form.

For 2% solids in water, overhead mixers and stirrers provide fewer coarse fibers than in the 1% solids in water, and high shear devices, such as a blender, produce a fine fiber that is relatively more coarse than that produced in the 1% solids in water.

For 4% solids in water, relatively higher shear devices, such as a blender, produce fine fibers that are relatively more coarse than the fine fibers produced in the 1% solids in water.

Increasing percent solids in water beyond 4% may require an increase in temperature to achieve fiber formation. Percent solids in water greater than 4% are advantageous for increased throughput and therefore lower cost of production.

In one embodiment, mixing the crosslinked gel with a water-miscible solvent to provide fibers comprises mixing a 1 or 2% solids in water with an overhead mixer or stirrer. In another embodiment, mixing the crosslinked gel with a water-miscible solvent to provide fibers comprises mixing 4% solids in water with a blender. For large scale production alternative mixing equipment with suitable mixing capacities are used.

Fibers formed from the mixing step are treated with a second crosslinking agent in a mixture of water and a water miscible solvent in suitable proportions so that the fibers do not lose their fiber form and form a gel. The resultant crosslinked fibers (e.g., surface crosslinked fibers) are then washed with a water-miscible solvent and air dried or oven dried below 80° C. to provide the mixed polymer composite fibers.

The second crosslinking agent is effective in further crosslinking (e.g., surface crosslinking) the mixed polymer composite fibers. Suitable second crosslinking agents include crosslinking agents that are reactive towards hydroxyl groups and carboxyl groups. The second crosslinking agent can be the same as or different from the first crosslinking agent. Representative second crosslinking agents include the metallic crosslinking agents noted above useful as the first crosslinking agents.

The second crosslinking agent can be applied at a relatively higher level than the first crosslinking agent per unit mass of fiber. This provides a higher degree of crosslinking on the surface of the fiber relative to the interior of the fiber. As described above, metal crosslinking agents form crosslinks between carboxylate anions and metal atoms or hydroxyl oxygen and metal atoms. These crosslinks can migrate from one oxygen atom to another when the mixed polymer fiber absorbs water and forms a gel. However, having a higher level of crosslinks on the surface of the fiber relative to the interior provides a superabsorbent fiber with a suitable balance in free swell, centrifuge retention capacity, absorbency under load for aqueous solutions and lowers the gel blocking that inhibits liquid transport.

The second crosslinking agent is applied in an amount from about 0.1 to about 20% by weight based on the total weight of mixed polymer composite fibers. The amount of second crosslinking agent applied to the polymers will vary depending on the crosslinking agent. The product fibers have an aluminum content of about 0.04 to about 2.0% by weight based on the weight of the mixed polymer composite fiber for aluminum crosslinked fibers, a titanium content of about 1.0 to about 4.5% by weight based on the weight of the mixed polymer composite fiber for titanium crosslinked fibers, a zirconium content of about 0.09 to about 6.0% by weight based on the weight of the mixed polymer composite fiber for zirconium crosslinked fibers; and a bismuth content of about 0.09 to about 5.0% by weight based on the weight of the mixed polymer composite fiber for bismuth crosslinked fibers.

The second crosslinking agent may be the same as or different from the first crosslinking agent. Mixtures of two or more crosslinking agents in different ratios may be used in each crosslinking step.

The preparation of representative mixed polymer composite fibers are described in Examples 1-3.

The absorbent properties of the representative mixed polymer composite fibers are summarized in the Table 1. In Table 1, "DS" refers to the carboxymethyl cellulose (CMC) degree of substitution, viscosity (cps) refers to Brookfield viscosity determined with spindle #3 at 20 rpm at 25° C., "$Al_2(SO_4)_3$," refers to aluminum sulfate octadecahydrate and "iPrOH" refers to isopropanol. The percentages of the CMC, starch, and first and second crosslinking agents refers to the percent by weight of each component based on the total weight of the product.

Test Methods

Free Swell and Centrifuge Retention Capacities

The materials, procedure, and calculations to determine free swell capacity (g/g) and centrifuge retention capacity (CRC) (g/g) were as follows.

Test Materials:

Japanese pre-made empty tea bags (available from Drugstore.com, IN PURSUIT OF TEA polyester tea bags 93 mm×70 mm with fold-over flap. (http:www.mesh.ne.jp/tokiwa/)).

Balance (4 decimal place accuracy, 0.0001 g for air-dried superabsorbent polymer (ADS SAP) and tea bag weights), timer; 1% saline; drip rack with clips (NLM 211); and lab centrifuge (NLM 211, Spin-X spin extractor, model 776S, 3,300 RPM, 120 v).

Test Procedure:

1. Determine solids content of ADS.
2. Pre-weigh tea bags to nearest 0.0001 g and record.
3. Accurately weigh 0.2025 g±0.0025 g of test material (SAP), record and place into pre-weighed tea bag (air-dried (AD) bag weight). (ADS weight+AD bag weight=total dry weight).
4. Fold tea bag edge over closing bag.
5. Fill a container (at least 3 inches deep) with at least 2 inches with 1% saline.
6. Hold tea bag (with test sample) flat and shake to distribute test material evenly through bag.
7. Lay tea bag onto surface of saline and start timer.
8. Soak bags for specified time (e.g., 30 minutes).
9. Remove tea bags carefully, being careful not to spill any contents from bags, hang from a clip on drip rack for 3 minutes.
10. Carefully remove each bag, weigh, and record (drip weight).
11. Place tea bags onto centrifuge walls, being careful not to let them touch and careful to balance evenly around wall.

12. Lock down lid and start timer. Spin for 75 seconds.
13. Unlock lid and remove bags. Weigh each bag and record weight (centrifuge weight).

Calculations:

The tea bag material has an absorbency determined as follows:

Free Swell Capacity, factor=5.78
Centrifuge Capacity, factor=0.50
Z=Oven dry SAP wt (g)/Air dry SAP wt (g)
Free Capacity (g/g):

$$\frac{[(\text{drip wt}(g) - \text{dry bag wt}(g)) - (AD\ SAP\ \text{wt}(g))] - (\text{dry bag wt}(g) * 5.78)}{(AD\ SAP\ \text{wt}(g) * Z)}$$

Centrifuge Retention Capacity (g/g):

$$\frac{[\text{centrifuge wt}(g) - \text{dry bag wt}(g) - (AD\ SAP\ \text{wt}(g))] - (\text{dry bag wt}(g) * 0.50)}{(AD\ SAP\ \text{wt} * Z)}$$

The following examples are provided for the purpose of illustrating, not limiting, the invention.

EXAMPLES

Example 1

The Preparation of Representative Mixed Polymer Composite Fibers; Aluminum Sulfate Crosslinking In this example, the preparation of representative mixed polymer composite fibers crosslinked with aluminum sulfate is described.

Corn starch (Clinton 185®, Archer Daniel Midland, Ill.) (1.8 g) was cooked for 45 minutes at 75° C. in 58 mL deionized water. The cooked starch was then added to 892 mL deionized water in a Hobart mixer. Then, carboxymethyl cellulose (30 g OD northern pine wood pulp CMC, DS 0.93, 1% aqueous solution, Brookfield viscosity 1350 cps, spindle #3 and speed 20 rpm) was added with mixing. The aqueous polymer mixture was mixed for 60 minutes.

To the aqueous polymer mixture was added 0.8 g aluminum sulfate octadecahydrate (Sigma Aldrich, WI) in deionized water. The polymer mixture was then mixed for 30 minutes to provide a crosslinked polymer gel.

The crosslinked polymer gel was then transferred to a Waring blender. Isopropanol (500 mL) was added and the combination mixed at 3000 rpm for 2 minutes. An additional 2.5 L isopropanol was added and the combination mixed for 1 minute at 2500 rpm. The resulting fiber slurry was collected by filtration.

The fiber slurry was added to a solution of aluminum sulfate octadecahydrate (2.2 g) (Sigma Aldrich, WI) in 50 mL water and 4 L 75% isopropanol and mixed for 15 minutes. The fiber slurry was collected by filtration and the collected fibers stirred in 1 L 95% isopropanol for 2 minutes. The product fibers were collected by filtration and air dried. The fibers had free swell (49.0 g/g) and centrifuge retention capacity (33.3 g/g) for 0.9% saline solution.

Example 2

The Preparation of Representative Mixed Polymer Composite Fibers: Aluminum Sulfate Crosstinking In this example, the preparation of representative mixed polymer composite fibers crosslinked with aluminum sulfate is described.

Corn starch (Clinton 185®, Archer Daniel Midland, Ill.) (1.2 g) was cooked for 45 minutes at 75° C. in 50 mL deionized water. The cooked starch was then added to 900 mL deionized water in a Hobart mixer. Then, carboxymethyl cellulose (20 g OD northern pine wood pulp CMC, DS 0.93, 1% aqueous solution, Brookfield viscosity 1350 cps, spindle #3 and speed 20 rpm) was added with mixing. The aqueous polymer mixture was mixed for 60 minutes.

To the aqueous polymer mixture was added 0.6 g aluminum sulfate octadecahydrate (Sigma Aldrich, WI) in deionized water. The polymer mixture was then mixed for 30 minutes to provide a crosslinked polymer gel.

The crosslinked polymer gel was then transferred to a Waring blender. Isopropanol (500 mL) was added and the combination mixed at 3000 rpm for 2 minutes. An additional 2.6 L isopropanol was added and the combination mixed for 1 minute at 2500 rpm. The resulting fiber slurry was collected by filtration.

The fiber slurry was added to a solution of aluminum sulfate octadecahydrate (1.6 g) (Sigma Aldrich, WI) in 50 mL water and 4 L 75% isopropanol and mixed for 15 minutes. The fiber slurry was collected by filtration and the collected fibers stirred in 1 L 95% isopropanol for 1 minute. The product fibers were collected by filtration and air dried. The fibers had free swell (49.7 g/g) and centrifuge retention capacity (34.5 g/g) for 0.9% saline solution.

Example 3

The Preparation of Representative Mixed Polymer Composite Fibers: Aluminum Sulfate Crosslinking In this example, the preparation of representative mixed polymer composite fibers crosslinked with aluminum sulfate is described.

Corn starch (Clinton 185®, Archer Daniel Midland, Ill.) (0.6 g) was cooked for 45 minutes at 75° C. in 31 mL deionized water. The cooked starch was then added to 919 mL deionized water in a Hobart mixer. Then, carboxymethyl cellulose (10 g OD northern pine wood pulp CMC, DS 0.93, 1% aqueous solution, Brookfield viscosity 1350 cps, spindle #3 and speed 20 rpm) was added with mixing. The aqueous polymer mixture was mixed for 60 minutes.

To the aqueous polymer mixture was added 0.4 g aluminum sulfate octadecahydrate (Sigma Aldrich, WI) in deionized water. The polymer mixture was then mixed for 30 minutes to provide a crosslinked polymer gel.

The crosslinked polymer gel was then transferred to a Waring blender. Isopropanol (500 mL) was added and the combination mixed at 3000 rpm for 2 minutes. An additional 2.5 L isopropanol was added and the combination mixed for 1 minute at 2500 rpm. The resulting fiber slurry was collected by filtration.

The fiber slurry was added to a solution of aluminum sulfate octadecahydrate (1.4 g) (Sigma Aldrich, WI) in 50 mL water and 4 L 75% isopropanol and mixed for 15 minutes. The fiber slurry was collected by filtration and the collected fibers stirred in 1 L 95% isopropanol for 1 minute. The product fibers were collected by filtration and air dried. The fibers had free swell (44.0 g/g) and centrifuge retention capacity (26.3 g/g) for 0.9% saline solution.

TABLE 1

Composition and Absorbent Properties of Precipitated Superabsorbent Fiber From Crosslinked Aqueous Mixtures of CMC and Starch

| Sample | CMC (DS, viscosity, %) | Starch (%) | First crosslinking agent (%) | Second crosslinking agent (%) | Fiber forming solvent | Free Swell (g/g) | CRC (g/g) |
|---|---|---|---|---|---|---|---|
| 1 | 1.03, 1465, 88.2 | 5.3 | $Al_2(SO_4)_3$ 1.80% | $Al_2(SO_4)_3$ 4.70% | iPrOH | 33.4 | 18.3 |
| 2 | 1.03, 1465, 88.2 | 5.3 | $Al_2(SO_4)_3$ 1.80% | $Al_2(SO_4)_3$ 4.70% | iPrOH | 43.7 | 26.0 |
| 3 | 0.93, 1370, 90.1 | 5.4 | $Al_2(SO_4)_3$ 1.20% | $Al_2(SO_4)_3$ 3.30% | iPrOH | 49.0 | 33.3 |
| 4 | 0.93, 1370, 89.7 | 5.4 | $Al_2(SO_4)_3$ 1.30% | $Al_2(SO_4)_3$ 3.60% | iPrOH | 49.7 | 34.5 |
| 5 | 0.93, 1370, 87.0 | 5.3 | $Al_2(SO_4)_3$ 1.70% | $Al_2(SO_4)_3$ 6.00% | iPrOH | 44.0 | 26.3 |

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for making mixed polymer composite fibers, comprising:
    (a) blending a carboxyalkyl cellulose and a starch in water to provide an aqueous gel; the starch being a cook or pregeletanized starch having only amylose and amylopectin polysaccharides,
    (b) treating the aqueous gel with a first crosslinking agent to provide a crosslinked gel;
    (c) mixing the crosslinked gel with a water-miscible solvent to provide fibers; and
    (d) treating the fibers with a second crosslinking agent to provide crosslinked mixed polymer composite fibers.

2. The method of claim 1 further comprising fiberizing the crosslinked mixed polymer composite fibers to provide fiberized crosslinked mixed polymer composite fibers.

3. The method of claim 2 further comprising drying the fiberized fibers to provide dried crosslinked mixed polymer composite fibers.

4. The method of claim 1, wherein the carboxyalkyl cellulose has a degree of carboxyl group substitution of from about 0.3 to about 2.5.

5. The method of claim 1, wherein the carboxyalkyl cellulose is carboxymethyl cellulose.

6. The method of claim 1, wherein the starch is selected from the group consisting of corn, wheat, maize, rice, sorghum, potato, cassava, barley, buckwheat, millet, oat, arrowroot, beans, peas, rye, tapioca, sago, and amaranth starches.

7. The method of claim 1, wherein the aqueous gel comprises from about 60 to about 99 percent by weight carboxyalkyl cellulose based on the total weight of mixed polymer composite fibers.

8. The method of claim 1, wherein the aqueous gel comprises from about 1 to about 20 percent by weight starch based on the total weight of mixed polymer composite fibers.

9. The method of claim 1, wherein the aqueous gel comprises from about 1 to about 20 percent by weight starch based on the total weight of mixed polymer composite fibers.

10. The method of claim 1, wherein the first crosslinking agent is a carboxyl group crosslinking agent.

11. The method of claim 1, wherein the first crosslinking agent is a hydroxyl group crosslinking agent.

12. The method of claim 1, wherein the first crosslinking agent is selected from the group consisting of aluminum (III) compounds, titanium (IV) compounds, bismuth (III) compounds, boron (III) compounds, and zirconium (IV) compounds.

13. The method of claim 1, wherein the first crosslinking agent is applied in an amount from about 0.1 to about 20 percent by weight based on the total weight of mixed polymer composite fibers.

14. The method of claim 1, wherein the water-miscible solvent is an alcohol.

15. The method of claim 1, wherein the water-miscible solvent is selected from the group consisting of methanol, ethanol, isopropanol, and mixtures thereof.

16. The method of claim 1, wherein the volume of water-miscible solvent to water is from about 1:1 to about 1:5.

17. The method of claim 1, wherein mixing the gel with the water-miscible solvent comprises stirring to provide fibers.

18. The method of claim 1, wherein the second crosslinking agent is selected from the group consisting of aluminum (III) compounds, titanium (IV) compounds, bismuth (III) compounds, boron (III) compounds, and zirconium (IV) compounds.

19. The method of claim 1, wherein the second crosslinking agent is applied in an amount from about 0.1 to about 20 percent by weight based on the total weight of crosslinked fibers.

* * * * *